United States Patent
Weger et al.

(10) Patent No.: US 6,617,599 B2
(45) Date of Patent: Sep. 9, 2003

(54) APPARATUS AND METHOD FOR AUTOMATED INDEXING OF A NUCLEAR GAUGE

(75) Inventors: Donald Erwin Weger, Knightdale, NC (US); John Norman Pjura, Durham, NC (US); Neal C. Harrington, Raleigh, NC (US); William F. Troxler, Jr., Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 09/773,681

(22) Filed: Jan. 31, 2001

(65) Prior Publication Data

US 2003/0141464 A1 Jul. 31, 2003

Related U.S. Application Data

(60) Provisional application No. 60/178,922, filed on Feb. 1, 2000.

(51) Int. Cl.$^7$ ................................. G01F 15/52
(52) U.S. Cl. ................ 250/498.1; 250/497.1; 250/252.1; 250/308; 250/390 D; 250/390 E; 378/207; 378/56; 378/89; 364/571; 364/414
(58) Field of Search .................... 250/252.1, 390 D, 250/390 E, 308, 497.1, 494.1, 498.1; 378/56, 89, 207; 364/571, 414

(56) References Cited

U.S. PATENT DOCUMENTS

| | | | |
|---|---|---|---|
| 2,781,453 A | | 2/1957 | Belcher et al. |
| 3,544,793 A | | 12/1970 | Bless et al. |
| 4,406,947 A | * | 9/1983 | Burton et al. ............ 250/252.1 |
| 4,465,929 A | * | 8/1984 | Edgar ...................... 250/252.1 |
| 4,524,279 A | * | 6/1985 | Christianson et al. .... 250/497.1 |
| 4,587,623 A | * | 5/1986 | Regimand et al. ......... 364/571 |
| 4,791,656 A | | 12/1988 | Pratt, Jr. et al. |
| 5,923,726 A | | 7/1999 | Regimand |
| 6,050,725 A | | 4/2000 | Regimand et al. |
| 6,369,381 B1 | * | 4/2002 | Troxler et al. ........... 250/252.1 |

FOREIGN PATENT DOCUMENTS

| | | |
|---|---|---|
| WO | WO 00/45159 | 8/2000 |

\* cited by examiner

*Primary Examiner*—John R. Lee
*Assistant Examiner*—David A. Vanore
(74) *Attorney, Agent, or Firm*—Alston & Bird LLP

(57) ABSTRACT

The invention provides a method and apparatus for facilitating calibration of a nuclear gauge by automating the movement of a source rod between a plurality of source rod positions. The apparatus can include a linearly moveable member, such as a threaded rod, a motorized linear actuator, such as a stepper motor, and a source rod grip attached to the linearly moveable member for affixing the source rod to the member.

31 Claims, 3 Drawing Sheets

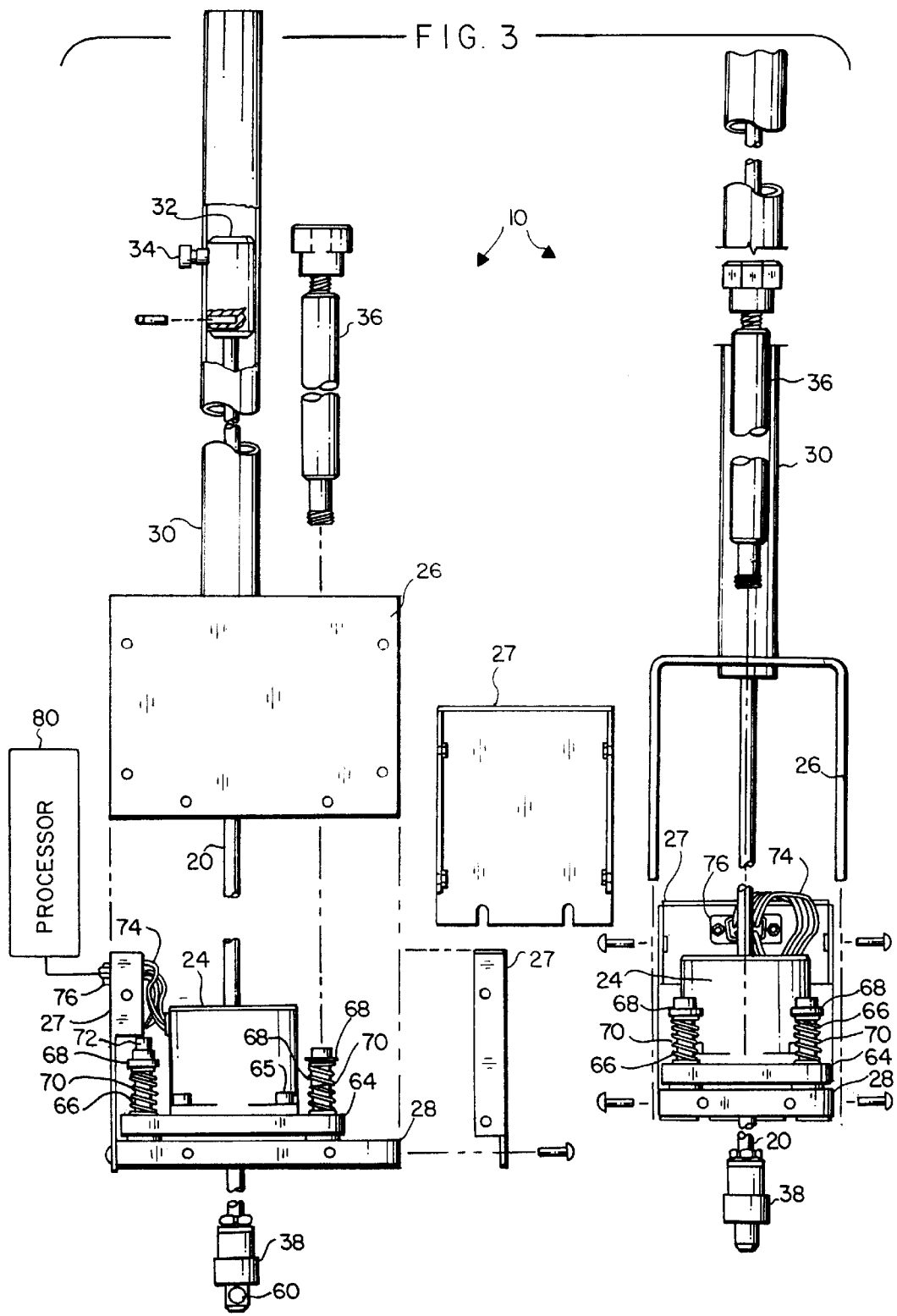

APPARATUS AND METHOD FOR AUTOMATED INDEXING OF A NUCLEAR GAUGE

CROSS-REFERENCE TO RELATED APPLICATIONS

This application claims the benefit of U.S. Provisional Application No. 60/178,922, filed Feb. 1, 2000, which is incorporated by reference herein in its entirety.

FIELD OF THE INVENTION

The present relates to apparatus for measuring the density of materials and, more particularly, relates to an apparatus and method for automating the calibration process of such density-measuring apparatus.

BACKGROUND OF THE INVENTION

Nuclear radiation gauges have been widely used for measuring the density of soil and asphaltic materials. Such gauges typically include a source of gamma radiation which directs gamma radiation into the test material, and a radiation detector located adjacent to the surface of the test material for detecting radiation scattered back to the surface. From this detector reading, a determination of the density of the material can be made. Examples of such gauges are described in U.S. Pat. No. 2,781,453 and U.S. Pat. No. 3,544,793, both of which are incorporated by reference herein in their entirety.

Nuclear density gauges currently in use, for example, the Troxler Model 3400 and 4400 series gauges manufactured by the assignee of the present invention, employ a nuclear radiation source, typically a mono-energetic source, that discharges gamma radiation into the test specimen and a radiation detector, typically a Geiger Mueller tube, that measures the scattered radiation. The gamma radiation interacts with matter in the test specimen, either by losing energy and changing direction (Compton interactions) or by terminating (photoelectric interactions). Consequently, the gamma radiation detected by the radiation detector has a continuous energy spectrum.

These gauges are designed to operate both in a "backscatter" mode and in a direct transmission mode. The radiation source is vertically moveable from a backscatter position where it resides within the gauge housing to a series of direct transmission positions where it is inserted into small holes or bores in the test specimen. The gamma radiation received by the radiation detector is related to the density of the test medium by an expression of the following form.

$$CR = A\exp(-BD) - C \qquad \text{Equation 1}$$

where:
- CR=count ratio (the accumulated photon count normalized to a reference standard photon count for purposes of eliminating long term effects of source decay and electronic drift),
- D=density of test specimen, and
- A, B, and C are constants.

The gauges are factory calibrated to arrive at values for constants A, B, and C for each gauge at each source depth position. The factory calibration procedure is a time-consuming iterative process, which may require several hours, or even days, to complete. In order to determine values for the three calibration parameters of the above equation, count measurements must be taken using at least three materials of different densities at each radiation source position. Typically, the three materials are solid blocks of aluminum, magnesium and a laminate of magnesium and aluminum. In some instances, as many as five calibration blocks of material have been employed in order to take into account the distinct mass attenuation coefficients of different soils. Thus, the standard factory calibration methods, often referred to as the three-block or five-block calibration methods, require a large number of individual counts in order to complete the calibration. For example, a gauge having a twelve-inch radiation source rod with seven different radiation source depth positions requires a minimum of twenty-one separate counts using the three-block calibration method. Each count is taken for a predetermined period of time, with longer periods of time producing greater precision. For example, for some gauge models, a typical count period for calibration is about four minutes for a direct transmission mode and about eight to twenty minutes for backscatter mode. Once all the counts are accumulated, values for the calibration parameters A, B, and C are calculated for each radiation source position.

The above-described calibration method is both time consuming and labor intensive because it requires numerous counts and movement of the gauge to positions overlying a plurality of blocks. To better automate the process and remove the need for numerous blocks, an automated calibration apparatus and method has been developed and described in PCT Publication No. WO 00/45159, assigned to the assignee of the present invention. The PCT application, which is incorporated herein by reference in its entirety, describes a calibration apparatus capable of simulating a plurality of densities at each radiation source depth, eliminating the need for movement of the gauge from block to block. However, there remains a need in the art for a method of further automating the calibration process.

SUMMARY OF THE INVENTION

The present invention facilitates automation of the calibration process for a nuclear gauge by allowing the source rod to be moved from one predetermined source rod position to the next without manual repositioning of the source rod by the user. When used in conjunction with an automated calibration apparatus, the present invention enables full automation of the calibration process.

The apparatus is advantageously used with a nuclear gauge, wherein the gauge comprises a gauge housing, a longitudinally moveable source rod extending into said gauge housing and including a handle affixed to a distal end thereof, the handle having a cavity therethrough and including an indexer, and an index rod extending through the cavity in the handle and affixed within the gauge housing. The index rod includes a plurality of notches positioned for engagement with the indexer of the handle, each notch corresponding to a predetermined source rod position. A source rod grip can be temporarily affixed to the source rod and operatively connected to a motorized linear actuator such that linear motion may be imparted to the source rod grip. In a preferred embodiment, the linear actuator is affixed to the index rod of the gauge.

One embodiment of the apparatus of the invention comprises a linearly moveable member, such as a threaded rod, and a motorized linear actuator, such as a stepper motor, operatively connected to the linearly moveable member for imparting linear motion to the member. The invention further includes a source rod grip attached to the linearly moveable member for affixing the source rod to the member.

Use of a linearly moveable member is a convenient method of connecting the linear actuator to the source rod grip so that linear motion may be imparted to the source rod grip and, consequently, to the source rod itself. As would be understood, the source rod grip can be configured for affixation directly to the source rod or to any part affixed to the source rod, such as a handle.

The apparatus may further comprise a tube operatively positioned to house a distal end of the linearly moveable member. The tube has a linear notch extending in the direction of travel of the linearly moveable member. A pin is affixed to the distal end of the linearly moveable member. The pin extends through the notch, thereby preventing axial rotation of the distal end of the linearly moveable member. This is a particularly useful embodiment wherein the linearly moveable member is a threaded rod.

A preferred embodiment of the source rod grip comprises a first vice jaw and a second vice jaw. The two vice jaws are attached and slidably engaged so that the vice jaws may be spaced apart. There is at least one pin affixed to each vice jaw and operatively positioned to grip the handle of a source rod of a nuclear gauge. The source rod grip further includes a tightening screw threaded into the vice jaws for adjusting the spacing therebetween.

A mounting plate can be affixed to the motorized linear actuator, the mounting plate having at least one hole therethrough. The apparatus can further include an enclosure surrounding the linear actuator, the enclosure including a bottom plate having one or more posts affixed thereto. The posts have a flanged end distal from the bottom plate that pass through the holes in the mounting plate. Thus, the mounting plate is moveable between the bottom plate and the flanged end of the post. Springs are mounted around the posts between the mounting plate and the flanged end of the post such that the mounting plate is biased towards the bottom plate. A switch is positioned to engage the mounting plate when the spring is substantially compressed against the flanged end of the post.

A processor is preferably connected to the motorized linear actuator. The processor may include an instruction set. A preferred instruction set includes a first instruction to raise the source rod grip until the indexer of the handle rises from a notch corresponding to a first predetermined source rod position to a position above a notch corresponding to a second predetermined source rod position, and a second instruction to lower the source rod grip until the indexer of the handle engages the notch corresponding to the second predetermined source rod position.

In operation, the invention enables a source rod of a nuclear gauge to be moved into a plurality of source rod positions. As noted above, the method and apparatus of the invention are particularly well-suited for use with a nuclear gauge comprising a longitudinally moveable source rod and an index rod adjacent thereto. In the method of the invention, the source rod is temporarily affixed into a first predetermined source rod position and a source rod grip is attached to the source rod. The source rod grip is moved using a linear actuator such that the source rod is temporarily affixed in a second predetermined source rod position. This moving step can be repeated in order to temporarily affix the source rod in each remaining source rod position.

If the gauge includes a handle affixed to the source rod, wherein the handle includes an indexer operatively positioned for engaging the notches of the index rod in order to temporarily affix the source rod in one of the predetermined positions, the moving step may include raising the source rod grip using the linear actuator such that the indexer is positioned above the notch in the index rod corresponding to a second predetermined source rod position. The source rod grip is then lowered using the linear actuator until the indexer is engaged with the notch in the index rod corresponding to the next determined source rod position. If the linear actuator is mounted on a moveable plate, the method may further include continuing to attempt to lower the source rod grip after the indexer is engaged with the notch, thereby raising the moveable plate from an initial position to a second position. The linear actuator stops when the moveable plate contacts a switch position to engage the moveable plate at the second position.

BRIEF DESCRIPTION OF THE DRAWINGS

Figure 2:
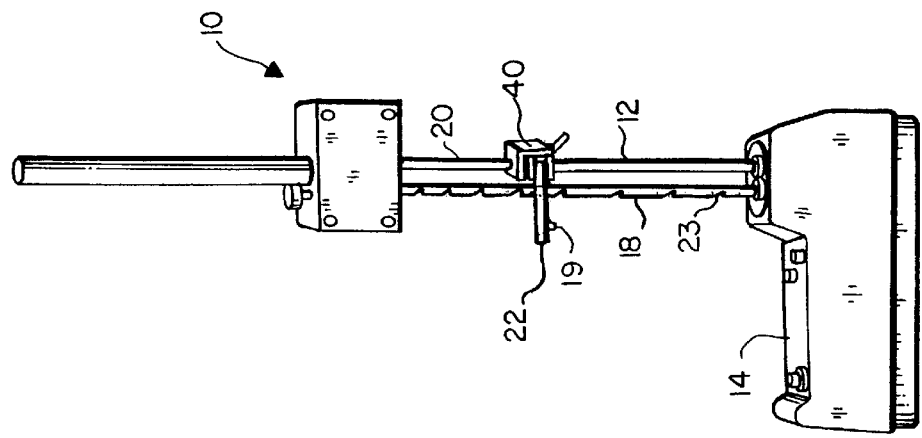
Figure 1:
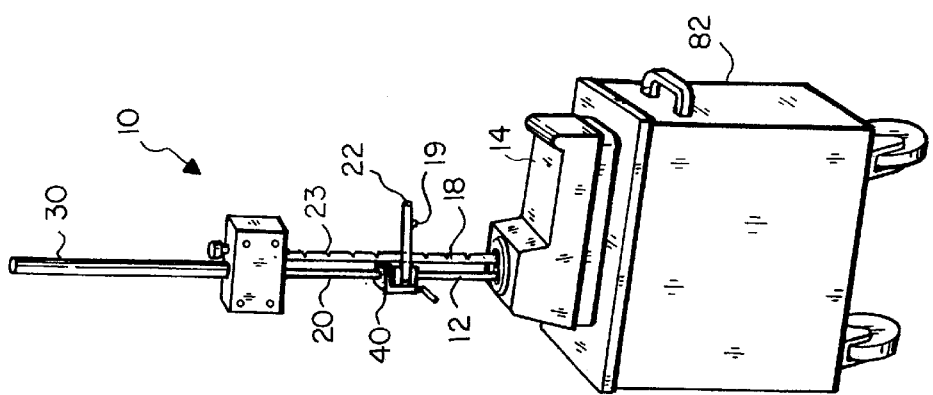
Figure 4:
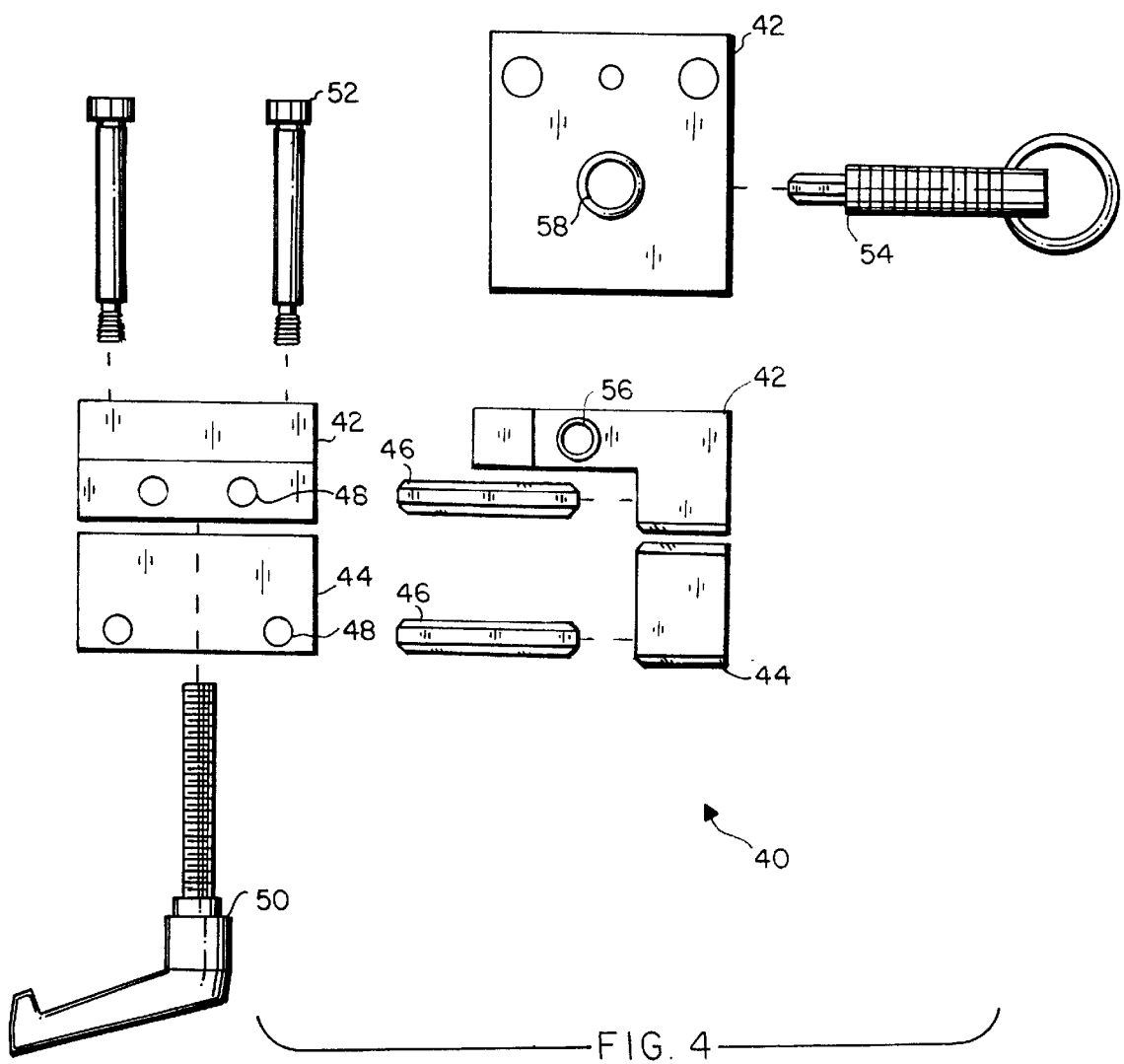

Having thus described the invention in general terms, reference will now be made to the accompanying drawings, which are not necessarily drawn to scale, and wherein:

FIG. 1 is a perspective view of the apparatus of the present invention attached to a nuclear gauge, the gauge being positioned on a calibration tool;

FIG. 2 is a perspective view of the apparatus of the present invention attached to a nuclear gauge;

FIG. 3 is a front and side view of a portion of the apparatus of the present invention; and FIG. 4 is a front, side and top view of the source rod grip portion of the apparatus of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention provides an apparatus 10 for moving or indexing the source rod 12 of a nuclear gauge 14 into a plurality of predetermined source rod positions. The apparatus 10 of the present invention is shown attached to a nuclear gauge 14 in FIGS. 1 and 2.

The apparatus 10 of the present invention can be adapted for use with many types and configurations of nuclear gauges, such as the Troxler Model 3400 and 4400 series gauges. Typically, these gauges can operate in both backscatter and direct transmission modes. In a preferred embodiment, the gauge that is used with the present invention includes a vertically moveable source rod 12 containing a radiation source (not shown) in a distal end thereof The radiation source may be any suitable radiation source, such as $^{137}Cs$ radiation source. The source rod extends into a vertical cavity in the gauge housing. One or more radiation detectors (not shown) are placed within the gauge housing. The radiation detector may be any type of gamma ray radiation detector known in the art. Preferably, the radiation detector is a Geiger Mueller tube.

The gauge 14 also includes means for vertically extending and retracting the source rod 12 to a plurality of predetermined source rod positions so as to change the spatial relationship between the radiation source and the radiation detector. The predetermined positions may include, for example, a backscatter position as well as a plurality of direct transmission positions, wherein the radiation source is positioned below the base of the gauge housing. Preferably, the means for extending and retracting comprise an index rod 18 operatively positioned adjacent to the source rod 12 and affixed within the gauge housing. The index rod 18 includes a plurality of notches 23. Each notch 23 corresponds to a predetermined source rod position. For example, one notch corresponds to the "safe" position wherein the radiation source is raised and shielded from the test material. The safe position is used to determine the standard count. Another notch corresponds to the backscatter mode wherein the radiation source is located adjacent to the surface of the test material underlying the gauge 14.

The means for vertically extending and retracting the source rod 12 also includes a handle 22 affixed to the source rod. The index rod 18 extends into a cavity in the handle 22. The handle 22 comprises a spring-loaded indexer (not shown) operatively positioned for engaging the notches 23 of the index rod 18 in order to temporarily affix the source rod 12 in one of the predetermined positions. The indexer can be disengaged from a notch by a trigger 19 extending from the handle 22. The notches 23 of the index rod 18 are typically shaped such that the indexer of the handle 22 remains securely engaged with the notch when downward pressure is applied to the handle (assuming the trigger 19 is not operated while the pressure is applied). Upward pressure on the handle 22 typically results in disengagement of the indexer from the notch, even when the trigger 19 is not utilized, due to the sloped upper surface of the notch.

FIG. 3 illustrates a preferred embodiment of the apparatus 10 of the present invention. As shown, the apparatus 10 preferably includes a linearly moveable member 20. The linearly moveable member 20 provides a convenient connection between the source rod grip 40 and the linear actuator 24 (both discussed below) in order to facilitate the transfer of linear motion to the source rod 12. The linearly moveable member 20 may comprise any type of rod or chain capable of pulling and/or pushing the source rod 12 of a nuclear gauge 14 into predetermined source rod positions. Preferably, the linearly moveable member 20 is a threaded rod, meaning a rod that is threaded along at least a portion of its length.

A motorized linear actuator 24 is operatively connected to the linearly moveable member 20 such that the actuator may impart linear motion to the member. The term "motorized" is intended to include any mechanical and/or electrical device capable of imparting linear motion. For example, in a preferred embodiment, the actuator 24 is a stepper motor, such as the Model No. 23A-6108A stepper motor manufactured by American Precision Industries of Buffalo, N.Y. Preferably, the linear actuator 24 is reversible such that the actuator can impart linear motion in both directions.

If the linearly moveable member 20 is a threaded rod, the actuator 24 preferably includes a rotatable component (not shown) having a threaded cavity therethrough. The threaded rod 20 is threaded through the threaded cavity such that rotatable component engages the threads of the rod. In this manner, rotation of the rotatable component will impart motion to the threaded rod 20. To prevent the rod 20 from simply spinning without linear movement, the apparatus 10 preferably includes means for immobilizing a distal end of the rod such that rotation of the rotatable component of the actuator 24 imparts linear motion to the rod.

As shown in FIG. 3, the apparatus 10 includes an enclosure surrounding the actuator 24 that includes a top cover 26, a bottom plate 28, and side plates 27. A tube 30 is preferably affixed to the top cover 26 and positioned to house a distal end of the threaded rod 20. The tube 30 has a notch therein extending linearly in the direction of travel of the rod 20. The end of the rod 20 is affixed to a plug 32. The plug 32 has a pin 34, such as a shoulder screw, affixed thereto and extending through the notch in the tube 30. The pin 34 prevents rotation of the rod 20 and allows the actuator 24 to impart linear motion to the rod.

The apparatus 10 also includes a connector 36 for affixing the apparatus to the index rod 18 of the gauge 14. The connector 36 may comprise, for example, a bolt that passes through the enclosure of the actuator 24 and screws into the distal end of the index rod 18. The index rod 18 provides a convenient and stable location for affixation of the linear actuator 24.

As shown in FIG. 3, a coupling member 38 is attached to the other distal end of the linearly moveable member 20. The coupling member 38 is designed to connect the linearly moveable member 20 to the source rod grip 40 illustrated in FIG. 4 and described below.

Now referring to FIG. 4, the apparatus 10 of the present invention further comprises a source rod grip 40. The grip 40 may comprise any type of coupling mechanism capable of temporarily affixing to the source rod 12 or any part affixed thereto. Preferably, the grip 40 is designed to accommodate different source rod 12 or handle 22 sizes. In one embodiment, the source rod grip 40 is designed to temporarily affix the source rod 12, or the handle 22 affixed to the source rod, in a vice-like grip. The source rod grip 40 is operatively connected to the linear actuator 24 so that linear motion may be imparted to the source rod grip and, consequently, to the source rod 12. As noted above, the source rod grip 40 can be temporarily affixed directly to the source rod 12 or to any part attached to the source rod, such as the handle 22.

In the embodiment shown in FIG. 4, the grip 40 comprises a first vice jaw 42 and a second vice jaw 44. The two vice jaws, 42 and 44, are attached in a manner that allows one or both of the vice jaws to slide relative to the other so that the two vice jaws may be spaced apart. For example, shoulder bolts 52 may be used to allow the two vice jaws, 42 and 44, to be slidably engaged.

The source rod grip 40 further includes at least one pin 46 inserted into a hole 48 in each vice jaw and affixed therein. Preferably, two pins 46 are affixed to each vice jaw, 42 and 44, as shown in FIG. 4. The pins 46 are positioned to grip the source rod 12 or the handle 22 of the gauge 14. A tightening screw 50 is threaded into both vice jaws, 42 and 44. The screw 50 may be tightened or loosened to adjust the spacing between the vice jaws, 42 and 44, and, consequently, the grip of the pins 46 on the source rod 12 or handle 22.

The first vice jaw 42 has a cavity 58 for receiving the coupling member 38 attached to the linearly moveable member 20. Preferably, the coupling member 38 is dimensioned for insertion into the cavity 58 and comprises a hole 60, as shown in FIG. 3. The hole 60 in the coupling member 38 facilitates attachment of the coupling member to the source rod grip 40. Referring back to FIG. 4, a connector 54, such as a spring-loaded plunger, is inserted into hole 56 in the first vice jaw 42 for securing the coupling member 38 to the source rod grip 40. The connector 54 secures the coupling member 38 to the source rod grip 40 by engaging the hole 60 in the coupling member.

In a preferred embodiment, the actuator 24 is mounted on a mounting plate 64. As shown in FIG. 3, the actuator 24 may be mounted using screws 65. The mounting plate 64 has at least one hole therethrough. A post 66, having a first end affixed to the bottom plate 28 and a second flanged end 68, passes through the hole in the mounting plate 64. Thus, the mounting plate 64 may freely move between the bottom plate 28 and the flanged end 68 of the post 66. As would be understood, the flanged end 68 of the post 66 may be created using a separate flange piece or as a part of a single-piece design of the post 66. Preferably, there are four posts 66 spaced around the periphery of the actuator 24. A spring 70 is mounted around each post 66 between the flanged end 68 of the post and the mounting plate 64 such that the spring biases the mounting plate toward the bottom plate 28. A switch 72 is positioned between the posts 66 such that the mounting plate 64 will engage the switch when the mounting plate has substantially fully compressed the spring 70 against the flanged end 68 of the post 66. In other words, the switch 72 will be engaged by the mounting plate 64 when the mounting plate has traveled a certain distance from the bottom plate 28. The exact distance is not critical to the present invention.

A processor 80 is preferably connected to the actuator 24 and the switch 72 for communication therewith. For example, as shown in FIG. 3, the wiring 74 from the switch 72 and actuator 24 may be connected to a port 76. The processor 80 preferably connects to the port 76. The processor 80 may comprise hardware, software or a combination thereof. Preferably, the processor 80 includes an instruction set that communicates the distance that the linearly moveable member 20 (and consequently the radiation source rod 12) should move to the actuator 24. The processor 80 preferably includes a first instruction to raise the source rod grip 40 until the indexer of the handle 22 rises from a notch corresponding to a first predetermined source rod position to a position above a notch corresponding to a second predetermined source rod position, and a second instruction to lower the source rod grip until the indexer of the handle engages the notch corresponding to the second predetermined source rod position.

As shown in FIG. 1, the apparatus 10 of the present invention may be used in concert with a calibration tool 82 in order to more fully automate the calibration process for a nuclear gauge. For example, the calibration tool 82 may comprise standardized calibration blocks, such as magnesium and aluminum blocks, or an automated calibration tool, such as the apparatus described in PCT Publication No. WO 00/45159. Preferably, if the apparatus 10 is used in conjunction with a calibration tool 82, the processor 80 is operatively connected to both the gauge 14 and the apparatus of the present invention such that the calibration of the gauge may be coordinated with operation of the apparatus of the present invention. Further, if an automated calibration tool 82 is used, the calibration tool itself is also preferably connected to the processor 80 such that the operation of all devices (gauge, calibration tool, and apparatus of the present invention) may be coordinated during the calibration process.

In operation, a nuclear gauge 14 is placed on a calibration tool 82. The source rod 12 of the gauge 14 is temporarily affixed in one of the predetermined source rod positions. The source rod grip 40 of the apparatus 10 of the present invention is attached to the source rod 12 or handle 22 of the gauge 14. The coupling member 38 of the linearly moveable member 20 is attached to the source rod grip 40 so that the linearly moveable member is attached to the source rod 12 of the gauge 14. The motorized linear actuator 24 is then used to impart linear movement to the linearly moveable member 20 and the source rod grip 40 such that the source rod 12 is moved to a second predetermined source rod position.

Preferably, the source rod 12 is placed in the lowest predetermined source rod position (i.e. the position corresponding to the lowest notch 23 in the index rod 18). If the gauge is to be calibrated, one or more counts are recorded at this source rod position and used to calculate new constants A, B and C in Equation 1. Thereafter, the apparatus 10 is used to raise the source rod 12 to the next higher source rod position. Again, one or more counts are recorded at the new source rod position for calibration purposes. Thereafter, the source rod is raised to the next higher source rod position and the above process is repeated.

To ensure that the source rod is firmly secured in the notch on the index rod 18 corresponding to the desired source rod position, the following procedure is preferably used. The actuator 24 raises the linearly moveable member 20 until the indexer of the handle 22 is positioned above the notch corresponding to the desired source rod position. As noted above, the notches in the index rod 18 are shaped such that the source rod 12 may be raised without first disengaging the indexer from the notch. Thus, by simply pulling upward on the source rod 12 (or handle 22), the linearly moveable member 20 can raise the source rod. Once the indexer is positioned above the desired notch, the actuator 24 reverses direction in order to lower the linearly moveable member 20 and the attached source rod 12. As the source rod 12 is lowered, the indexer engages the notch, which is shaped to prevent further downward movement by the indexer without disengaging the indexer using the trigger 19. Once downward movement of the indexer is prevented by the notch, the linearly moveable member 20 will be unable to travel downward, thereby causing the moveable plate 64 to move upward as the actuator 24 continues to operate. When the moveable plate, 64 engages the switch 72, the actuator 24 receives a signal to stop. In this manner, the apparatus 10 of the present invention ensures that the source rod 12 is firmly secured in each source rod position. Once the actuator 24 is once again activated to raise the source rod 12 to the next higher source rod position, the moveable plate 64 will return to its initial position adjacent to the bottom plate 28.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for moving a source rod of a nuclear gauge from one source rod position to a second source rod position, comprising:
   a linearly moveable member;
   a motorized linear actuator operatively connected to said linearly moveable member for imparting linear motion to said member; and
   a source rod grip attached to said linearly moveable member and operatively positioned for affixation of the source rod to said member.

2. An apparatus according to claim 1, wherein said linearly moveable member comprises a threaded rod, the threads of said rod being engaged with said linear actuator.

3. An apparatus according to claim 2, further comprising:
a tube operatively positioned to house a distal end of said threaded rod, said tube having a linear notch therein extending in the direction of travel of the linearly moveable threaded rod; and
a pin affixed to said distal end of said threaded rod and extending through said notch, thereby preventing axial rotation of said distal end of said rod.

4. An apparatus according to claim 1, wherein said motorized linear actuator comprises a stepper motor.

5. An apparatus according to claim 1, wherein said source rod includes a handle affixed thereto and said source rod grip comprises:
a first vice jaw;
a second vice jaw attached to said first vice jaw and slidably engaged therewith such that the vice jaws may be spaced apart;
at least one pin affixed to said first vice jaw; and
at least one pin affixed to said second vice jaw, wherein said pins are operatively positioned to grip the handle of the source rod.

6. An apparatus according to claim 5, wherein said source rod grip further comprises a tightening screw threaded into both of said vice jaws for adjusting the spacing between said vice jaws.

7. An apparatus according to claim 1, further comprising:
a mounting plate affixed to said motorized linear actuator, said mounting plate having at least one hole therethrough;
an enclosure surrounding said motorized linear actuator, said enclosure comprising a bottom plate;
a post having a first end affixed to said bottom plate and a second flanged end, said post passing through said hole of said mounting plate such that said mounting plate is moveable between said bottom plate and said flanged end of said post;
a spring mounted around said post between said mounting plate and said flanged end of said post, said spring operatively positioned to bias said mounting plate toward said bottom plate; and
a switch positioned to engage said mounting plate when said spring is substantially compressed against said flanged end.

8. An apparatus according to claim 1, further comprising a processor operatively connected to said motorized linear actuator.

9. An apparatus according to claim 8, wherein said processor includes an instruction set, the instruction set comprising instructions to raise and lower the linearly moveable member.

10. An apparatus for moving a source rod of a nuclear gauge from one source rod position to a second source rod position, comprising:
a linearly moveable threaded rod having a first end, said first end having a pin affixed thereto;
a tube operatively positioned to house said first end of said threaded rod, said tube having a linear notch therein extending in the direction of travel of the linearly moveable threaded rod, said pin of said rod extending through said notch, thereby preventing axial rotation of said first end of said rod;
a motorized linear actuator engaged with the threads of said rod for imparting linear motion to said rod; and
a source rod grip attached to said linearly moveable member and operatively positioned for affixation of the source rod to said member.

11. An apparatus according to claim 10, wherein a handle is affixed to said source rod and said source rod grip comprises:
a first vice jaw;
a second vice jaw attached to said first vice jaw and slidably engaged therewith such that the vice jaws may be spaced apart;
at least one pin affixed to said first vice jaw;
at least one pin affixed to said second vice jaw, wherein said pins are operatively positioned to grip the handle of the source rod; and
a tightening screw threaded into both of said vice jaws for adjusting the spacing between said vice jaws.

12. An apparatus according to claim 10, further comprising:
a mounting plate affixed to said motorized linear actuator, said mounting plate having at least one hole therethrough;
an enclosure surrounding said motorized linear actuator, said enclosure comprising a bottom plate;
a post having a first end affixed to said bottom plate and a second flanged end, said post passing through said hole of said mounting plate such that said mounting plate is moveable between said bottom plate and said flanged end of said post;
a spring mounted around said post between said mounting plate and said flanged end of said post, said spring operatively positioned to bias said mounting plate toward said bottom plate; and
a switch positioned to engage said mounting plate when said spring is substantially compressed against said flanged end.

13. An apparatus for moving a source rod of a nuclear gauge from one source rod position to a second source rod position, comprising:
a nuclear gauge, said gauge comprising:
a gauge housing,
a longitudinally moveable source rod extending into said gauge housing and including a handle affixed to a distal end thereof, the handle having a cavity therethrough and including an indexer, and
an index rod extending through the cavity in said handle and affixed within said gauge housing, said index rod including a plurality of notches positioned for engagement with said indexer, each notch corresponding to a predetermined source rod position;
a source rod grip temporarily affixed to said source rod; and
a motorized linear actuator operatively connected to said source rod grip for imparting linear motion to said source rod grip.

14. An apparatus according to claim 13, wherein said source rod grip is temporarily affixed to said handle of said source rod.

15. An apparatus according to claim 13, wherein said motorized linear actuator is a stepper motor.

16. An apparatus according to claim 13, wherein said motorized linear actuator is affixed to said index rod of said nuclear gauge.

17. An apparatus according to claim 13, further comprising a linearly moveable member operatively engaged with said linear actuator for imparting linear motion to said member, said source rod grip being affixed to said linearly moveable member.

18. An apparatus according to claim 17, wherein said linearly moveable member is a threaded rod, the threads of said rod being engaged with said linear actuator.

19. An apparatus according to claim 18, further comprising:
    a tube operatively positioned to house a distal end of said threaded rod, said tube having a linear notch therein extending in the direction of travel of the linearly moveable threaded rod; and
    a pin affixed to said distal end of said threaded rod and extending through said notch, thereby preventing axial rotation of said distal end of said rod.

20. An apparatus according to claim 13, wherein said source rod grip comprises:
    a first vice jaw;
    a second vice jaw attached to said first vice jaw and slidably engaged therewith such that the vice jaws may be spaced apart;
    at least one pin affixed to said first vice jaw; and
    at least one pin affixed to said second vice jaw, wherein said pins are operatively positioned to grip the handle of the source rod.

21. An apparatus according to claim 20, wherein said source rod grip further comprises a tightening screw threaded into both of said vice jaws for adjusting the spacing between said vice jaws.

22. An apparatus according to claim 13, further comprising a processor operatively connected to said motorized linear actuator.

23. An apparatus according to claim 22, wherein said processor includes an instruction set, the instruction set comprising:
    a first instruction to raise the source rod grip until said indexer of said handle rises from a notch corresponding to a first predetermined source rod position to a position above a notch corresponding to a second predetermined source rod position; and
    a second instruction to lower the source rod grip until said indexer of said handle engages the notch corresponding to the second predetermined source rod position.

24. A method of moving a source rod of a nuclear gauge from one source rod position to a second source rod position, comprising:
    providing a nuclear gauge, said gauge comprising a longitudinally moveable source rod and an index rod adjacent to the source rod, the index rod including a plurality of notches, each notch corresponding to a predetermined source rod position;
    temporarily affixing the source rod in a first predetermined source rod position;
    attaching a source rod grip to the source rod of the nuclear gauge, the source rod grip being operatively connected to a motorized linear actuator; and
    moving the source rod grip using the linear actuator such that the source rod is temporarily affixed in a second predetermined source rod position.

25. A method according to claim 24, further comprising repeating said moving step in order to temporarily affix the source rod in each remaining source rod position.

26. A method according to claim 24, wherein the first predetermined source rod position is the lowest predetermined source rod position.

27. A method according to claim 24, wherein the gauge further comprises a handle affixed to the source rod, the handle having a cavity therethrough and including an indexer operatively positioned for engaging the notches of the index rod in order to temporarily affix the source rod in one of the predetermined positions, and said moving step comprises:
    raising the source rod grip using the linear actuator such that the indexer is positioned above the notch in the index rod corresponding to the second predetermined source rod position; and
    lowering the source rod grip using the linear actuator until the indexer is engaged with the notch in the index rod corresponding to the second predetermined source rod position.

28. A method according to claim 27, wherein the linear, actuator is mounted on a moveable plate, and said method further comprises:
    continuing to attempt to lower the source rod grip using the linear actuator after the indexer is engaged with the notch such that the moveable plate is raised from an initial position to a second position; and
    stopping the linear actuator when the moveable plate contacts a switch positioned to engage the moveable plate at the second position.

29. A method according to claim 24, further comprising the step of obtaining at least one calibration count at each of the first and second predetermined source rod positions.

30. A method of moving a source rod of a nuclear gauge into a plurality of source rod positions, comprising:
    providing a nuclear gauge, said gauge comprising a longitudinally moveable source rod, a handle affixed to the source rod, and an index rod adjacent to the source rod, wherein the index rod including a plurality of notches, each notch corresponding to a predetermined source rod position, and wherein the handle comprises an indexer operatively positioned for engaging the notches of the index rod in order to temporarily affix the source rod in one of the predetermined positions;
    temporarily affixing the source rod in a first predetermined source rod position;
    attaching a source rod grip to the handle of the nuclear gauge, the source rod grip being affixed to a threaded rod, the threads of said rod being engaged with a linear actuator;
    raising the threaded rod using the linear actuator such that the indexer is positioned above the notch in the index rod corresponding to a second predetermined source rod position; and
    lowering the threaded rod using the linear actuator until the indexer is engaged with the notch in the index rod corresponding to the second predetermined source rod position.

31. A method according to claim 30, wherein the linear actuator is mounted on a moveable plate, and said method further comprises:
    continuing to attempt to lower the threaded rod using the linear actuator after the indexer is engaged with the notch, thereby raising the moveable plate from an initial position to a second position; and
    stopping the linear actuator when the moveable plate contacts a switch positioned to engage the moveable plate at the second position.

* * * * *

UNITED STATES PATENT AND TRADEMARK OFFICE
CERTIFICATE OF CORRECTION

PATENT NO. : 6,617,599 B2 Page 1 of 1
APPLICATION NO. : 09/773681
DATED : September 9, 2003
INVENTOR(S) : Weger et al.

It is certified that error appears in the above-identified patent and that said Letters Patent is hereby corrected as shown below:

<u>Title page,</u>

(*) Notice: should appear as follows,

--Subject to any disclaimer, the term of this patent is extended or adjusted under 35

U.S.C. 154(b) by 390 days.--.

Signed and Sealed this

Seventeenth Day of July, 2007

JON W. DUDAS
*Director of the United States Patent and Trademark Office*